United States Patent
Simpson et al.

(10) Patent No.: US 9,624,512 B2
(45) Date of Patent: Apr. 18, 2017

(54) ALCOHOL PRODUCTION PROCESS

(71) Applicant: LanzaTech New Zealand Limited, Roselle, IL (US)

(72) Inventors: Sean Dennis Simpson, Auckland (NZ); Joseph Henry Tizard, Auckland (NZ)

(73) Assignee: LANZATECH NEW ZEALAND LIMITED, Auckland (NZ)

(*) Notice: Subject to any disclaimer, the term of this patent is extended or adjusted under 35 U.S.C. 154(b) by 620 days.

(21) Appl. No.: 13/847,707

(22) Filed: Mar. 20, 2013

(65) Prior Publication Data
US 2013/0280694 A1 Oct. 24, 2013

Related U.S. Application Data

(63) Continuation of application No. 13/058,629, filed on Apr. 27, 2011, now abandoned.

(60) Provisional application No. 61/148,282, filed on Jan. 29, 2009, provisional application No. 61/259,887, filed on Nov. 10, 2009.

(30) Foreign Application Priority Data

Jan. 29, 2010 (WO) ............... PCT/NZ2010/000009

(51) Int. Cl.
C12P 7/06 (2006.01)
(52) U.S. Cl.
CPC ............ *C12P 7/065* (2013.01); *Y02E 50/17* (2013.01)
(58) Field of Classification Search
None
See application file for complete search history.

(56) References Cited

U.S. PATENT DOCUMENTS

| 5,173,429 A | 12/1992 | Gaddy et al. |
| 5,593,886 A | 1/1997 | Gaddy |
| 5,807,722 A | 9/1998 | Gaddy |
| 5,821,111 A | 10/1998 | Grady et al. |
| 6,136,577 A | 10/2000 | Gaddy |
| 6,340,581 B1 | 1/2002 | Gaddy |
| 6,368,819 B1 | 4/2002 | Gaddy et al. |

(Continued)

FOREIGN PATENT DOCUMENTS

| WO | 0208438 | 1/2002 |
| WO | 2007117157 | 10/2007 |

(Continued)

OTHER PUBLICATIONS

Phillips, J.R., et al "Synthesis gas as substrate for the biological production of fuels and chemicals" Applied Biochemistry and Biotechnology, 1994, 45/46. pp. 145-157.

(Continued)

*Primary Examiner* — Blaine Lankford
*Assistant Examiner* — Lauren K Van Buren
(74) *Attorney, Agent, or Firm* — Frank S Molinaro

(57) ABSTRACT

The invention relates to the production of products such as alcohols and acids by microbial fermentation, particularly microbial fermentation of substrates comprising CO. It more particularly relates to methods and systems for improving efficiency of products by microbial fermentation. In particular embodiments, the invention provides a method of optimizing production of desired products including the step of ascertaining the proportion of CO converted to CO2.

10 Claims, 4 Drawing Sheets

(56) References Cited

U.S. PATENT DOCUMENTS

| | | |
|---|---|---|
| 6,753,170 B2 | 6/2004 | Gaddy et al. |
| RE39,175 E | 7/2006 | Gaddy et al. |
| 7,196,218 B2 | 3/2007 | Gaddy et al. |
| 7,285,402 B2 | 10/2007 | Gaddy et al. |
| 2003/0211585 A1* | 11/2003 | Gaddy .................. C12P 7/065 435/161 |

FOREIGN PATENT DOCUMENTS

| | | | |
|---|---|---|---|
| WO | WO2007117157 | * | 10/2007 |
| WO | 2008028055 | | 3/2008 |
| WO | WO2008115080 | * | 9/2008 |
| WO | 2008154301 | | 12/2008 |
| WO | 2009020747 | | 2/2009 |
| WO | 2009022925 | | 2/2009 |
| WO | 2009058028 | | 5/2009 |
| WO | 2009113878 | | 9/2009 |
| WO | 2010064932 | | 6/2010 |
| WO | 2010064933 | | 6/2010 |
| WO | 2010098679 | | 9/2010 |
| WO | 2011002318 | | 1/2011 |

OTHER PUBLICATIONS

Abrini J et al "*Clostridium autoethanogenum*, sp. Nov., an anaerobic bacterium that produces ethanol from carbon monoxide", Archives of Microbiology. 1994, vol. 161, pp. 345-351.

Ragsdale SW "Life with Carbon Monoxide", Critical Reviews in Biochemistry and Molecular Biology, 2004, 39, pp. 165-195.

Henstra et al. "Microbiology of Synthesis Gas Fermentation for Biofuel Production" Current Opinion in Biotechnology, 2007, 18, pp. 200-206.

* cited by examiner

ALCOHOL PRODUCTION PROCESS

CROSS REFERENCE TO RELATED APPLICATIONS

This application is a continuation of co-pending U.S. application Ser. No. 13/058,629 filed on Apr. 27, 2011 which is a National Stage of International Application No. PCT/NZ2010/000009, filed on Jan. 29, 2010, which claims priority to the following US Provisional Applications: U.S. Provisional Application No. 61/148,282 filed Jan. 30, 2009 and U.S. Provisional Application 61/259,887 filed Nov. 10, 2009. The contents of the prior applications mentioned above are incorporated herein by reference in their entirety.

FIELD OF THE INVENTION

This invention relates generally to methods for increasing the efficiency of microbial growth and production of products by microbial fermentation on gaseous substrates. More particularly the invention relates to processes for producing alcohols, particularly ethanol, by microbial fermentation of gases containing carbon monoxide. In particular embodiments, the invention relates to methods of determining the overall net conversion of CO to products during microbial fermentation.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to continue to grow sharply in future, due to an increased interest in ethanol in Europe, Japan, the USA and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, and the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium Ijungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is typically associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

Several enzymes known to be associated with the ability of micro-organisms to use carbon monoxide as their sole source of carbon and energy are known to require metal co-factors for their activity. Examples of key enzymes requiring metal cofactor binding for activity include carbon monoxide dehydrogenase (CODH), and acetyl-CoA synthase (ACS).

WO2007/117157, WO2008/115080, WO2009/022925, WO2009/058028, WO2009/064200, WO2009/064201 and WO2009/113878, the disclosure of which are incorporated herein by reference, describe processes that produce alcohols, particularly ethanol, by anaerobic fermentation of gases containing carbon monoxide. Acetate produced as a by-product of the fermentation process described in WO2007/117157 is converted into hydrogen gas and carbon dioxide gas, either or both of which may be used in the anaerobic fermentation process. WO2009/022925 discloses the effect of pH and ORP in the conversion of substrates comprising CO to products such as acids and alcohols by fermentation. WO2009/058028 describes the use of industrial waste gases for the production of products, such as alcohol, by fermentation. WO2009/064201 discloses carriers for CO and the use of CO in fermentation. WO2009/113878 discloses the conversion of acid(s) to alcohol(s) during fermentation of a substrate comprising CO.

Microbes capable of growing on CO-containing gases are known to do so at a slower rate than is traditionally associated with microbes grown on sugars. From a commercial perspective, in a fermentation process the time required for a microbial population to grow to a sufficiently high cell density to allow an economically viable level of product to be synthesised, is a key operating cost affecting the profitability of the process. Technologies that act to enhance culture growth rates and/or productivities and therefore reduce the time required to reach desired cell densities and/or desired product levels and may serve to improve the commercial viability of the overall process.

In fermentation processes dedicated to the production of alcohols from gaseous feedstocks, ensuring that the appropriate conditions for microbial growth and/or alcohol production, can be critical to maintaining optimal microbial growth and/or alcohol productivities. For example, during initial start-up of a fermentation, the primary goal may be microbial growth. However, when the desired microbial density is achieved, the primary goal may be alcohol production. Understanding how the product profile changes over the course of a fermentation, as the changes occur, particularly in response to changes in operating conditions can allow an operator to optimise productivity.

Providing a substrate comprising CO and optionally H2 at an optimum level, or within an optimum range for particular requirements, such as rapid growth and/or alcohol production, can also be challenging. For example, too much CO can lead to CO inhibition as described in U.S. Pat. No. 7,285,402, which is fully incorporated herein by reference. Furthermore, too little CO and metabolic rates including microbial growth and alcohol production, can decrease.

It is an object of the present invention to provide a process that goes at least some way towards overcoming the above disadvantages, or at least to provide the public with a useful choice.

SUMMARY OF THE INVENTION

The invention generally relates to a method for producing products including acids and/or alcohols by microbial fermentation of a substrate comprising CO, wherein at least a portion of a microbial culture converts: at least a portion of the substrate comprising CO to microbial biomass; and/or at least a portion of the substrate comprising CO to acid(s); and/or at least a portion of the substrate comprising CO to alcohol(s); and/or acid(s) and at least a portion of the substrate comprising CO to alcohol(s).

In one embodiment, the microbial culture converts:
at least a portion of the substrate comprising CO to acid(s); and
at least a portion of the substrate comprising CO to alcohol(s).

In another embodiment, the microbial culture converts:
at least a portion of the substrate comprising CO to acid(s); and
at least a portion of the substrate comprising CO to alcohol(s); and
acid(s) and at least a portion of the substrate comprising CO to alcohol(s).

In particular embodiments of the invention, the substrate comprises CO and H2. However, in accordance with the invention, the conversion proceeds with insufficient H2 for total carbon fixation into cell matter and/or products. In particular embodiments, H2 is provided such that less than 2:1 H2:CO is converted by the culture, such as approximately 1:1; or approximately 1:2; or approximately 1:3; or approximately 1:4; or approximately 1:5; or approximately 1:10. In particular embodiments, H2 is not provided.

In a first aspect of the invention, there is provided a method of improving efficiency of microbial fermentation of a substrate comprising CO and optionally H2, the method including providing the substrate to a microbial culture such that a first proportion of CO is fixed as one or more desired products including acid(s) and/or alcohol(s) and a second proportion of CO is converted to CO2. In particular embodiments, determination of the proportion of CO converted to CO2 is used to determine a substrate supply rate for production of the one or more desired products.

In particular embodiments, the substrate supply rate is either:
 i. increased if the proportion of CO converted to CO2 is determined to be below an optimal value or range; or
 ii. decreased if the proportion of CO converted to CO2 is determined to be above an optimal value or range; or
 iii. maintained if the proportion of CO converted to CO2 is determined to be substantially at an optimal value or range.

In particular embodiments, the substrate supply rate is automatically adjusted such that the proportion of CO converted to CO2 is maintained substantially at an optimal value or range.

In particular embodiments, the optimum value or range can be ascertained experimentally based on the desired fermentation products. In particular embodiments, wherein alcohol is the desired product, the substrate can be provided such that at least 50%, or at least 60%, or at least 70%, or at least 80%, or at least 90% of fixed carbon is fixed as alcohol. Additionally or alternatively, wherein the desired product is acetate, the substrate can be provided such that at least 50%, or at least 60%, or at least 70%, or at least 80%, or at least 90% of fixed carbon is fixed as acetate.

In particular embodiments, a proportion of carbon fixed as a desired product can be substantially maintained constant. In particular embodiments, wherein the proportion of carbon fixed as a desired product deviates from a pre-determined range, supply of the substrate is controlled such that the proportion is returned to the pre-determined range. In particular embodiments, the predetermined range is about ±1%, or about ±2%, or about ±3%, or about ±4%, or about ±5%.

In particular embodiments, substrate supply is automatically adjusted in response to deviations from the pre-determined range.

In a second aspect of the invention, there is provided a method of improving the efficiency of producing one or more acids and/or alcohols by microbial fermentation of a substrate comprising CO and optionally H2, wherein at least a portion of a microbial culture is transitioned from converting:

at least a portion of the substrate comprising CO to acid(s); or at least a portion of the substrate comprising CO to alcohol(s); or acid(s) and at least a portion of the substrate comprising CO to alcohol(s); to converting:

at least a portion of the substrate comprising CO to acid(s); or at least a portion of the substrate comprising CO to alcohol(s); or acid(s) and at least a portion of the substrate comprising CO to alcohol(s).

In particular embodiments of the invention, at least a portion of the microbial culture can be transitioned by making an adjustment to the microbial culture and/or the substrate stream. In certain embodiments, the anaerobic fermentation is carried out in a bioreactor, wherein the microbial culture is at least partially suspended in a fermentation broth comprising a liquid nutrient medium. In particular embodiments, at least a portion of the microbial culture can be transitioned by making an adjustment to the fermentation broth and/or liquid nutrient medium.

In certain embodiments, the adjustment includes one or more of: changing pH of the fermentation broth; changing redox potential of the fermentation broth; changing CO concentration of the fermentation broth; changing composition of the substrate stream; changing pressure of the substrate stream; altering fermentation broth agitation rate; product removal; changing acid and/or alcohol concentration of the fermentation broth; changing one or more nutrients in the liquid nutrient medium; changing rate of supply of one or more nutrients.

In particular embodiments of the invention, the substrate comprising CO also comprises H2. In some embodiments, the adjustment may include changing H2 concentration of the fermentation broth and/or changing the CO:H2 ratio in the fermentation broth. In certain embodiments, the substrate comprising CO and optionally H2 is gaseous. In some embodiments, the adjustment may include changing partial pressure of CO and/or H2 in the bioreactor.

In particular embodiments of the invention, the method includes determining the proportion of CO oxidised to CO2, such that a net conversion by the microbial culture can be determined. In particular embodiments, the overall net conversion of the microbial fermentation is:

at least a portion of the substrate comprising CO to acid(s); or at least a portion of the substrate comprising CO to alcohol(s); or acid(s) and at least a portion of the substrate comprising CO to alcohol(s).

In a third aspect, there is provided a method of improving the efficiency of producing one or more acids and/or alcohols by microbial fermentation of a substrate comprising CO under predetermined operating parameters, the method including determining a proportion of carbon directed towards one or more products and depending on the determination, either:

i. making an adjustment to one or more operating parameters, such that the proportion of carbon fixed as a desired product increases; or ii. maintaining the operating parameters, such that the proportion of carbon fixed as a desired product maintains substantially constant.

In certain embodiments, the adjustment includes changing one or more of the following operating parameters: changing pH of the fermentation broth; changing redox potential of the fermentation broth; changing CO concentration of the fermentation broth; changing rate of substrate supply, changing composition of the substrate stream; changing pressure of the substrate stream; altering fermentation broth agitation rate; product removal; changing acid and/or alcohol concentration of the fermentation broth; changing one or more nutrients in the liquid nutrient medium; changing rate of supply of one or more nutrients.

In particular embodiments of the invention, the substrate comprising CO also comprises H2. In some embodiments, the adjustment may include changing H2 concentration of the fermentation broth and/or changing the CO:H2 ratio in the fermentation broth. In certain embodiments, the substrate comprising CO and optionally H2 is gaseous. In some embodiments, the adjustment may include changing partial pressure of CO and/or H2 in the bioreactor.

In particular embodiments of the first, second and third aspects, the method of improving the efficiency includes improving a rate at which one or more products, such as alcohol, in particular ethanol, are produced.

In a fourth aspect of the invention, there is provided a method of determining an overall net conversion in a microbial fermentation of a substrate comprising CO, the method including determining the proportion of carbon fixed as a particular product by a microbial culture.

In particular embodiments, the proportion of carbon fixed as a particular product can be established by determining the proportion of CO oxidised to CO2.

In particular embodiments, the overall net conversion in the microbial fermentation is:

at least a portion of the substrate comprising CO to acid(s); or at least a portion of the substrate comprising CO to alcohol(s); or acid(s) and at least a portion of the substrate comprising CO to alcohol(s);

In particular embodiments, the proportion of CO converted to CO2 is determined by measuring CO and optionally H2 consumed by the microbial culture and the CO2 produced by the microbial culture.

In certain embodiments of the first, second, third or fourth aspects, the CO, H2 and/or CO2 entering and/or exiting the bioreactor can be monitored substantially continuously or at discrete time points, such as before and/or after an adjustment has been made. In some embodiments, the amounts of CO, CO2 and/or H2 entering and/or exiting the bioreactor can be determined using gas chromatography. In particular embodiments, gas chromatography is used to determine the proportion of CO converted to CO2. In one embodiment, the gas chromatography is conducted using a micro GC.

It is recognised that portions of the microbial culture may be involved with alternative conversions, however the overall net conversion by the whole culture can be determined. In particular embodiments of the invention wherein H2 is substantially limited, such as embodiments wherein a substrate stream comprises less than 5% H2; or less than 4% H2; or less than 3% H2; or less than 2% H2; or less than 1% H2; a $CO2_{produced}/CO_{consumed}$ ratio of 0.5 indicates a net conversion of a substrate comprising CO to acid(s) and optionally microbial cells. A $CO2_{produced}/CO_{consumed}$ ratio of 0.667 indicates a net conversion of a substrate comprising CO to alcohol(s). A $CO2_{produced}/CO_{consumed}$ of 0.5-0.667 indicates a net conversion of a substrate comprising CO to acid(s) and alcohol(s) and optionally microbial cells. A $CO2_{produced}/CO_{consumed}$ ratio over 0.667 indicates a net conversion of a substrate comprising CO and acid(s) to alcohol(s).

It is recognised that in various embodiments of the above aspects, at least a portion of the microbial culture may convert alcohol(s) to acid(s) and carbon monoxide. However, in particular embodiments, the anaerobic fermentation results in a net overall conversion of the substrate comprising CO to products. In other embodiments, wherein $CO2_{produced}/CO_{consumed}$ is less than 0.5, the net conversion is alcohol(s) to acid(s) and reduction of CO2 and/or H2O, which may be undesirable.

In a fifth aspect of the invention, there is provided a system for the microbial fermentation of a substrate stream comprising CO to products such as acid(s) and/or alcohol(s) comprising a bioreactor containing a microbial culture; measuring means adapted to determine a proportion of carbon fixed as a particular product and at least one adjustment means adapted to make one or more adjustments to the microbial culture and/or the substrate stream.

In particular embodiments, the measuring means includes at least one means adapted to determine the composition of an exhaust stream exiting the bioreactor and optionally the substrate stream entering the bioreactor. The measuring means may optionally be linked to a processing means such that a proportion of carbon fixed as a desired product can be determined. In one embodiment, the measuring means is a gas chromatograph.

In certain embodiments, the adjustment means are configured to make one or more adjustments if the determining means determines the proportion of carbon fixed as a desired product has deviated from a predetermined value or range. In particular embodiments, the adjustment means are configured to make adjustments by: changing pH of the fermentation broth; changing redox potential of the fermentation broth; changing CO concentration of the fermentation broth; changing H2 concentration of the fermentation broth; changing composition of the substrate stream; changing pressure of the substrate stream; fermentation broth agitation rate; product removal; changing acid and/or alcohol concentration of the fermentation broth; changing one or more nutrients in the liquid nutrient medium; changing rate of supply of one or more nutrients.

In particular embodiments, the system includes processing means adapted to control one or more adjustment means, such that one or more adjustment means, such that one or more adjustment(s) can be made to the microbial culture and/or substrate stream if it is determined that the proportion of carbon fixed as a desired product has deviated from a predetermined value or range. In other embodiments, the system may include visual and/or aural feedback to an operator, such that the operator can manually control the adjustment means.

In particular embodiments of the various aspects, the substrate comprises a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In a particular embodiment, the gaseous substrate comprises a gas obtained from a steel mill.

In certain embodiments the substrate comprises from 20% CO to 100% CO by volume, such as from 40% to 95% CO by volume, such as from 60% to 90% CO by volume, or such as from 70% to 90% CO by volume. In particular embodiments, the substrate comprises 25%, or 30%, or 35%, or 40%, or 45%, or 50% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. The gaseous substrate may also contain some $CO_2$ for example, such as about 1% to about 80% $CO_2$ by volume, or 1% to about 30% $CO_2$ by volume.

In particular embodiments of the various aspects, the substrate comprising CO is gaseous.

In particular embodiments, the alcohol produced by the fermentation process is ethanol. The fermentation reaction may also produce acetate.

In particular embodiments, the fermentation reaction is carried out by one of more strains of carboxydotrophic bacteria. Preferably, the carboxydotrophic bacterium is selected from *Clostridium*, *Moorella* and *Carboxydothermus*, such as *Clostridium autoethanogenum*, *Clostridium ljungdahlii*, *Clostridium ragsdalei*, *Clostridium carboxydivorans* and *Moorella thermoacetica*. In one embodiment, the carboxydotrophic bacterium is *Clostridium autoethanogenum*.

Although the invention is broadly as defined above, it is not limited thereto and also includes embodiments of which the following description provides examples.

BRIEF DESCRIPTION OF THE DRAWINGS

The invention will now be described in detail with reference to the accompanying Figures in which.

DETAILED DESCRIPTION OF THE INVENTION

Figure 1:
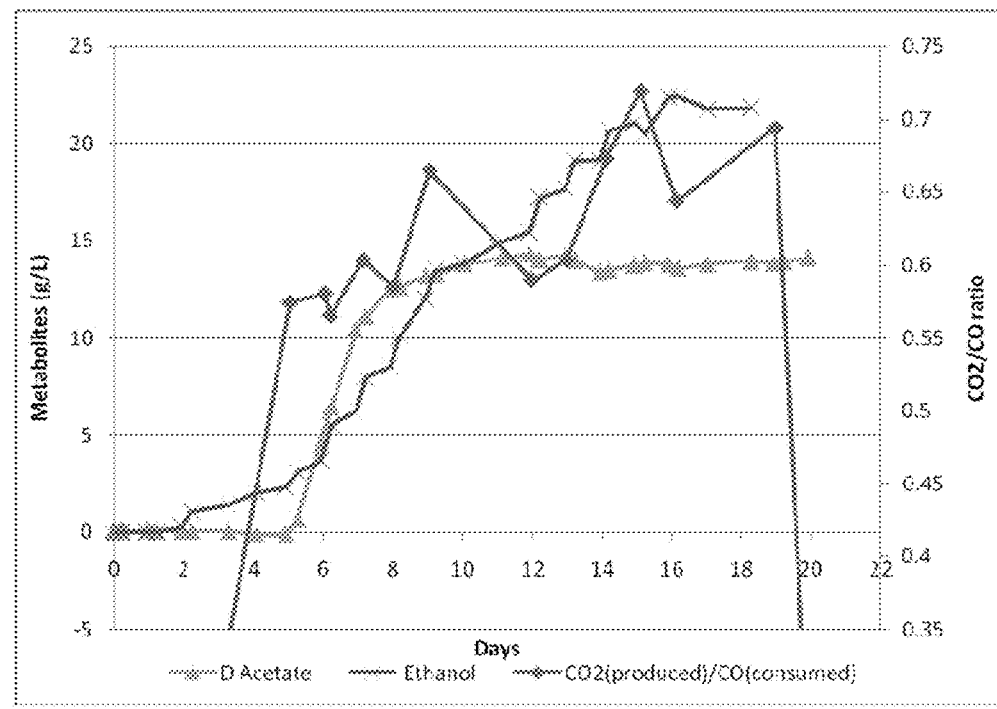
FIG. 1: is a graph showing changes in acetate and alcohol production and $CO2_{produced}/CO_{consumed}$ in a batch fermentation of a substrate comprising CO to produce products including alcohol.

Carboxydotrophic bacteria such as *Clostridium autoethanogenum* unexpectedly produce products such as acid(s) and alcohol(s) by anaerobic fermentation of a substrate comprising CO and optionally H2, by a number of different mechanisms simultaneously. It has been surprisingly recognised that acid(s) and alcohol(s) production by carboxydotrophic micro-organisms can occur without concomitant water production. In previously reported fermentation of substrates comprising CO and H2, products such as alcohols and/or acids are considered to be produced in concert with water. However, it has been surprisingly recognised that when insufficient H2 is available for complete carbon fixation into cellular matter and products, such as alcohols and/or acids, the fermentation proceeds without concomitant production of water. In particular embodiments, insufficient H2 is available for complete carbon fixation when H2 and CO are consumed by a microbial culture in a H2:CO ratio of less than 2:1; such as approximately 1:1; or approximately 1:2; or approximately 1:3; or approximately 1:4; or approximately 1:5; or approximately 1:10. In particular embodiments, H2 is substantially unavailable to the microbial culture.

Without wishing to be bound by theory, products such as acetate and ethanol are produced by at least one, or at least two, or at least three or all of the following mechanisms simultaneously:

1. Fixation of carbon monoxide to acetic acid $$2CO + 2H_2 \rightarrow CH_3COOH$$

2. Fixation of carbon monoxide to ethanol $$3CO + 3H_2 \rightarrow CH_3CH_2OH + CO_2$$

3. Reduction of acetic acid to ethanol $$CH_3COOH + H_2 \rightarrow CH_3CH_2OH + CO_2$$

4. Oxidation of ethanol to acetic acid $$CH_3CH_2OH + H_2O \rightarrow CH_3COOH + 2H_2$$

Anabolism or microbial cell mass accumulation typically occurs concomitantly with at least mechanism 1. However, it is considered only a small proportion of carbon is directed to anabolism compared to other metabolites.

In addition, the micro-organisms can effectively produce their own H2 through the water gas shift reaction ($CO + H_2O \rightarrow CO_2 + H_2$). Thus metabolites including acetate and ethanol are also produced in accordance with A-C:

$$4CO + 2H_2O \rightarrow CH_3COOH + 2CO_2 \quad \text{A)}$$

$$6CO + 3H_2O \rightarrow CH_3CH_2OH + 4CO_2 \quad \text{B)}$$

$$CH_3COOH + 2CO + H_2O \rightarrow CH_3CH_2OH + 2CO_2 \quad \text{C)}$$

It is recognised that the microbial culture is dynamic and without wishing to be bound by theory, it is considered the microbial culture converts at least a portion of a substrate comprising CO and optionally H2, to products according to one or more of 1-3 and A-C simultaneously. Thus, in the dynamic microbial culture, several different mechanisms may be occurring within the system to produce an overall net conversion of CO to alcohols and/or acids. To determine how CO is metabolised, the influence of H2 and the weighting of equations 1-3 relative to A-C needs to be determined. Once determined, the relative individual influence of equations 1-3 and A-C can be established by determining CO2 produced, and H2 and CO consumed.

According to one aspect of the invention, there is provided a method for producing products including acids and/or alcohols by microbial fermentation of a substrate comprising CO, wherein at least a portion of a microbial culture converts: at least a portion of the substrate comprising CO to acid(s) and microbial cells; and/or at least a portion of the substrate comprising CO to acid(s); and/or at least a portion of the substrate comprising CO to alcohol(s); and/or acid(s) and at least a portion of the substrate comprising CO to alcohol(s).

It has been surprisingly found that by determining the proportion of CO converted to CO2, a modelling system can be developed to predict the production profile of products, such as alcohol and/or acids, for a CO metabolising bacteria. Because the degree of oxidation in the products differs depending on whether the bacteria are synthesising organic acids or alcohols, the proportion of carbon the bacteria are devoting to solventogenesis (such as alcohol production) can be predicted based on the stoichiometry of the underlying chemical processes.

Understanding how the product profile of a system is changing allows for adjustments or alterations to be made to the operating conditions of a system to promote a desirable outcome, such as increased alcohol production. Furthermore, in a particular embodiment, the invention provides a method of improving efficiency of fermentation of a substrate comprising CO to produce products including alcohol(s) and/or acid(s), the method including providing a substrate at an optimum level or within an optimum range.

In particular embodiments wherein CO is provided in the absence of H2 or with limited amounts of H2, the influence of 1-3 will be minimal. It is considered that limited amounts of H2 are available when the proportion of H2 in a substrate stream is less than 5%; such as less than 4%; such as less than 3%; such as less than 2%; such as less than 1%. As such, the relative influence of equations A-C can be established by calculating a ratio of $CO2_{produced}/CO_{consumed}$ according to $y = 2/3x + 0.5$. In such embodiments, equation A will give a ratio of 0.5, equation B will give a ratio of 0.667, equation C will give a value of >0.667 and equation 4 will give a value of <0.5. From the calculated value, the relative influence of each equation can be determined.

The invention also provides a method of improving the efficiency of producing one or more acids and/or alcohols by microbial fermentation of a substrate comprising CO, wherein at least a portion of a microbial culture is transitioned from converting:

at least a portion of the substrate comprising CO to acid(s) and microbial cells; or at least a portion of the substrate comprising CO to acid(s); or at least a portion of the substrate comprising CO to alcohol(s); or acid(s) and at least a portion of the substrate comprising CO to alcohol(s);

to converting:

at least a portion of the substrate comprising CO to acid(s) and microbial cells; or at least a portion of the substrate comprising CO to acid(s); or at least a portion of the substrate comprising CO to alcohol(s); or acid(s) and at least a portion of the substrate comprising CO to alcohol(s).

DEFINITIONS

Unless otherwise defined, the following terms as used throughout this specification are defined as follows:

The terms "increasing the efficiency", "increased efficiency" and the like, when used in relation to a fermentation process, include, but are not limited to, increasing one or more of: the rate of growth of micro-organisms catalysing the fermentation, the volume of desired product (such as alcohols) produced per volume of substrate (such as carbon monoxide) consumed, the rate of production or level of production of the desired product, and the relative proportion of the desired product produced compared with other by-products of the fermentation.

The term "substrate comprising carbon monoxide" and like terms should be understood to include any substrate in which carbon monoxide is available to one or more strains of bacteria for growth and/or fermentation, for example.

"Gaseous substrate comprising carbon monoxide" include any gas which contains carbon monoxide. The gaseous substrate will typically contain a significant proportion of CO, preferably at least about 5% to about 100% CO by volume.

In the context of fermentation products, the term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system.

The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Membrane Reactor such as Hollow Fibre Membrane Bioreactor (HFMBR), Static Mixer, or other vessel or other device suitable for gas-liquid contact.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "overall net conversion" and the like, as used herein, is intended to describe the conversion of substrates, such as CO, to products including acid(s) and/or alcohol(s) by a microbial culture at a particular time point. It is recognised that portions of a microbial culture may be devoted to different functions at a particular time point and a number of products may be produced. Furthermore, one or more of the products present in the fermentation broth may be converted into other products. Accordingly, the overall net conversion includes all the products produced by the microbial culture at any particular point in time.

While the following description focuses on particular embodiments of the invention, namely the production of ethanol and/or acetate using CO as the primary substrate, it should be appreciated that the invention may be applicable to production of alternative alcohols and/or acids and the use of alternative substrates as will be known by persons of ordinary skill in the art to which the invention relates. For example, gaseous substrates containing carbon dioxide and hydrogen may be used. Further, the invention may be applicable to fermentation to produce butyrate, propionate, caproate, ethanol, propanol, and butanol. The methods may also be of use in producing hydrogen. By way of example, these products may be produced by fermentation using microbes from the genus *Moorella, Clostridia, Ruminococcus, Acetobacterium, Eubacterium, Butyribacterium, Oxobacter, Methanosarcina, Methanosarcina,* and *Desulfotomaculum.*

Certain embodiments of the invention are adapted to use gas streams produced by one or more industrial processes. Such processes include steel making processes, particularly processes which produce a gas stream having a high CO content or a CO content above a predetermined level (i.e., 5%). According to such embodiments, acetogenic bacteria are preferably used to produce acids and/or alcohols, particularly ethanol or butanol, within one or more bioreactors. Those skilled in the art will be aware upon consideration of the instant disclosure that the invention may be applied to various industries or waste gas streams, including those of vehicles with an internal combustion engine. Also, those skilled in the art will be aware upon consideration of the instant disclosure that the invention may be applied to other fermentation reactions including those using the same or different micro-organisms. It is therefore intended that the scope of the invention is not limited to the particular embodiments and/or applications described but is instead to be understood in a broader sense; for example, the source of the gas stream is not limiting, other than that at least a component thereof is usable to feed a fermentation reaction. The invention has particular applicability to improving the overall carbon capture and/or production of ethanol and other alcohols from gaseous substrates such as automobile exhaust gases and high volume CO-containing industrial flue gases.

Fermentation

Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is a gaseous substrate containing CO. The substrate may be a CO-containing waste gas obtained as a by-product of an industrial process, or from some another source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing substrate may be captured from the industrial process before it is emitted into the atmosphere, using any convenient method. Depending on the composition of the CO-containing substrate, it may also be desirable to treat it to remove any undesired impurities, such as dust particles before introducing it to the fermentation. For example, the gaseous substrate may be filtered or scrubbed using known methods.

Alternatively, the CO-containing substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 40% to 95% CO by volume, from 60% to 90% CO by volume, and from 70% to 90% CO by volume. In particular embodiments, the substrate comprises 25%, or 30%, or 35%, or 40%, or 45%, or 50% CO by volume. Substrates having lower concentrations of CO, such as 6%, may also be appropriate, particularly when $H_2$ and $CO_2$ are also present.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise up to 2:1, or 1:1, or 1:2 ratio of H2:CO. In other embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology Volume* 101, *Number* 3/October, 2002) could be used for this purpose.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/115157 and WO2008/115080 referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117,157 and WO08/115,080.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO07/117,157, WO08/115,080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and co-solvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Determining Carbon Fixation in Fermentation

By determining the proportion of CO converted to CO2, a modelling system has been devised to predict the production profile of products for a CO metabolising bacteria. Since the degree of oxidation in the products differs depending on whether the bacteria are synthesising organic acids or alcohols, the proportion of carbon the bacteria are devoting to solventogenesis can be predicted based on the stoichiometry of the underlying chemical processes. Analysis and/or quantification of the degree of oxidised by-products (CO2) effectively provides a real-time indication of the overall product conversion by a microbial culture:

The system models the state of the reactor as being a composite of one or more 'ideal' states as calculated from the underlying stoichiometry. The modelling system assigns a specific gas sample into a 'best fit' compromise between two primary states and a modifying condition that generates two secondary hybrid reactions depending on the available hydrogen, and two tertiary states.

The primary states are:
Fixation of carbon monoxide to acetic acid $$2CO + 2H_2 \rightarrow CH_3COOH \text{ (a } CO_2/CO \text{ ratio of 0)}$$

Fixation of carbon monoxide to ethanol $$3CO + 3H_2 \rightarrow CH_3CH_2OH + CO_2 \text{ (a } CO_2/CO \text{ ratio of } 0.3333)$$

In the absence of free hydrogen gas, both of these primary reactions are supplemented by a water-gas-shift reaction;

$$CO + H_2O \rightarrow H_2 + CO_2$$

It can be assumed this water-gas shift occurs simultaneously with carbon fixing when carbon fixing is carried out in the absence of free hydrogen.

Combining the water-gas-shift with the two primary reactions gives a pair of secondary hybrid reactions that occur in the absence of free hydrogen gas.

Fixation of carbon monoxide to acetic acid in the absence or free hydrogen $$4CO + 2H_2O \rightarrow CH_3COOH + 2CO_2 \text{ (a } CO_2/CO \text{ ratio of } 0.5)$$

Fixation of carbon monoxide to ethanol in the absence of free hydrogen $$6CO + 3H_2O \rightarrow CH_3CH_2OH + 4CO_2 \text{ (a } CO_2/CO \text{ ratio of } 0.6667)$$

Additionally there are two potential tertiary states;
Reduction of acetic acid to ethanol $$CH_3COOH + 2CO + H_2O \rightarrow CH_3CH_2OH + 2CO_2 \text{ (a } CO_2/CO \text{ ratio of } 1)$$

Oxidation of ethanol to acetic acid $$CH_3CH_2OH + H_2O \rightarrow CH_3COOH + 2H_2 \text{ (a } CO_2/CO \text{ ratio of } 0)$$

By observing the ratio of $CO_{2\ (produced)}/CO_{(consumed)}$, the state of the culture can be deduced and its product output calculated. In a culture with 100% hydrogen consuming character, the ratio is going to vary between 0 and $1/3$. This can be graphed as a linear function with the equation $y=1/3x$. In a culture with 100% water-gas-shift character, the ratio will vary between $1/2$ and $2/3$, which can likewise be graphed as a linear function with the equation $y=2/3x+0.5$.

When hydrogen consumption is negligible, the first linear function can effectively be ignored for modelling purposes and by solving only the second equation, using the observed $CO_2/CO$ value, the calculated x value will be the proportion of carbon directed into ethanol production. Subtracting total $CO_2$ released from total carbon intake will give the available carbon for fixing, multiplying this by the previously calculated proportion gives the predicted carbon fixed as ethanol. Since two carbon atoms are fixed into one molecule of ethanol, this value must be halved to convert Mol input carbon into Mol output ethanol.

When hydrogen consumption is non negligible but is insufficient for complete carbon fixation into products and/or cell matter, neither the CO2/CO ratio nor the amount of hydrogen can be used to directly infer the state of the culture. Ethanol production from hydrogen occupies a continuum between $$3CO + 3H_2 \rightarrow CH_3CH_2OH + CO_2 \text{ (a } CO_2/CO \text{ ratio of } 0.3333) \text{ and}$$

$$2CO + 2H_2 CH_3COOH \text{ (a } CO_2/CO \text{ ratio of } 0)$$

Both utilize CO and $H_2$ in a 1:1 ratio. Without knowing the position on this continuum occupied by the hydrogen consuming portion of the microbial culture, the relative output of $CO_2$ by the hydrogen consuming micro-organisms is unknown. An accurate overall $CO_2/CO$ ratio cannot be calculated without knowing the $CO_2$ produced by the underlying water gas shift utilizing population, and that figure cannot be calculated without first accurately knowing the $CO_2/CO$ ratio of the hydrogen consumers and the relative quantity of $CO_2$ they are producing.

However, this can be circumvented by considering that in a hydrogen consuming state, $H_2$ consumption equates to CO consumption and the second state equation can also be a $CO_2/H_2$ ratio, represented as a z value rather than an x value;

$$y=2/3x+0.5$$

and $$y=1/3z$$

However, without a third equation to link x and z, the simultaneous equation cannot be solved. Because the state of the culture can change, this third equation; $y=ax+bz$ is in fact, variable, as is to be expected given that the degree to which a culture produces acetate or ethanol during the course of a fermentation, changes with the conditions.

In the circumstance that a culture was totally consuming hydrogen, both the $CO_2/CO$ and $CO_2/H_2$ ratios would be equal, as CO consumption would be 1:1 with hydrogen consumption. From this it can be inferred that a line drawn between the a point calculated with the $CO_2/CO$ ratio and the $CO_2/H_2$ ratio will tend towards horizontal as the hydrogen consuming character of the microbial population increases, and that the z axis intercept would be directly proportional to the proportion of carbon being fixed into ethanol when the line was totally horizontal, as in a hydrogen eating state, $CO_2$ is produced on a 1:1 basis with ethanol.

From this information, an approximation can be added to allow the third 'hybrid' equation to be calculated.

The gradient of a line between the $CO_2/CO$ and $CO_2/H_2$ ratio is used to assign a weighting to the z intercept of this hybrid line; if this line was horizontal, the gradient $([CO_2/CO]/[CO_2/H_2])$ would be 1, indicating a pure hydrogen consuming culture, in which all ethanol production was coming from hydrogen consumers, meaning the only equation to consider is the hydrogen equation.

As this line moves away from horizontal, its gradient $([CO_2/CO]/[CO_2/H_2])$ will tend towards zero. Using this as a multiplicative weighting value to multiply by the z intercept, the inferred amount of $CO_2$ (and ethanol) produced by hydrogen consumers will likewise tend towards zero as the line between the $CO_2/CO$ and $CO_2/H_2$ ratios moves further and further away from horizontal.

The z intercept multiplied with the gradient derived weighting factor gives an approximation of the overall $CO_2$ produced by the hydrogen consuming microorganisms, and the CO consumed by the hydrogen consumers will be 1:1 with hydrogen consumption, and this value can then be substituted in to solve the equation $y=1/3x$. The CO consumed and $CO_2$ produced by hydrogen consuming microorganisms can be subtracted from the total consumption and production to give the remaining CO and $CO_2$ that the water-gas-shift population is responsible for, and the ratio of this remainder can be substituted in to solve the equation $y=2/3x+0.5$. Thus the proportion of carbon fixed into a particular product, such as acid(s) and/or alcohol(s) can be determined.

Those skilled in the art will appreciate that the amount of CO and optionally H2 consumed and CO2 produced can be monitored continuously or at discrete time points as desired.

Any means known in the art may be used to determine the amount of CO2, CO and H2; however in one embodiment of the invention, gas chromatography (GC) is used to measure the amount of CO2, CO and H2 present in an exhaust stream exiting a bioreactor. The proportion of carbon fixed as alcohol and/or acid can be calculated if the composition of the substrate stream entering the bioreactor is known. If the composition of the substrate stream is unknown, a further gas chromatograph can be used to determine composition. Other means for determining the amount of CO2 produced and substrate consumed include mass spectroscopy (MS), GCMS and inline sensors.

Thus, in accordance with the invention, the proportion of carbon fixed as a particular product such as acetate and/or ethanol can be determined by measuring CO2 produced, CO consumed and optionally H2 consumed. It is recognised that rate at which substrate (for example CO and optionally H2) is made available to a microbial culture can affect the relative proportion of products as well as the rate at which they are produced. For example, increasing substrate supply to an acetate producing culture can increase the proportion of carbon directed toward alcohol production.

A substrate comprising CO and optionally H2 is typically provided in gaseous form and availability of CO and H2 to a microbial culture will be dependent upon the mass transfer properties of the fermentation system. For example, availability of CO and/or H2 to a microbial culture suspended in a fermentation broth is dependent on factors known to those skilled in the art including temperature, broth composition, gas supply rate, gas composition, CO vapour pressure, H2 vapour pressure, mixing. Thus, increasing availability of CO and/or H2 to a microbial fermentation requires improving mass transfer properties of the system, such as increasing substrate supply rate and/or increasing agitation of a mechanically stirred bioreactor.

In accordance with the methods of the invention, efficiency of fermentation can be improved by providing substrate comprising CO and optionally H2 at or toward an optimum level or range. An optimum level can be ascertained based on the desired products of the fermentation. For example, if alcohol and microbial growth are desired, substrate comprising CO and optionally H2 can be supplied such that carbon is predominantly fixed as alcohol, while a portion is available for microbial growth. For example, a substrate comprising CO can be supplied to a microbial culture, such that microbial growth and alcohol production occur.

The conditions, particularly the substrate supply rate and/or relative CO and H2 concentrations, can be varied until microbial growth and alcohol production are optimised to the satisfaction of the operator. Since the influence each pathway of fixation of carbon into products can be determined, the substrate supply can be adjusted to attain and/or maintain the desirable conditions during fermentation. For example, it is recognised that a substrate stream may comprise fluctuating CO and/or H2 components. However, using the methods of the invention, the net production of products can be maintained at a substantially constant ratio by adjusting the substrate supply.

Additionally or alternatively, as a microbial culture grows, or the microbial density fluctuates, the substrate supply can be altered in accordance with the microbial cultures requirements based on determination of CO2 produced and CO and H2 consumed.

In this regard, the proportion of carbon directed toward a particular product can be maintained substantially constant despite changes to substrate supply and/or microbial density.

In particular embodiments of the invention, the proportion of carbon directed toward a particular product can be selected by an operator and the conditions adjusted to maintain the proportion substantially constant. For example, if an operator requires 90% of the fixed carbon to be directed toward ethanol production, substrate can be supplied such that the proportion does not deviate outside a predetermined range, such as ±1%, or ±2%, or ±3%, or ±4%, or ±5%. In particular embodiments, the substrate supply can be controlled in response to determination of the proportion of carbon directed to a particular product. In particular embodiments, the substrate supply is automatically adjusted in response to changes in the proportion of carbon directed to a particular product.

In particular embodiments, wherein CO is supplied in the absence of appreciable amounts of H2, a $CO2_{produced}/CO_{consumed}$ ratio can be determined. In particular embodiments of the invention, microbial growth and alcohol production may be optimised when acetate is concurrently produced. As such a $CO2_{produced}/CO_{consumed}$ ratio of <0.667, such as approximately 0.66, or approximately 0.65, or approximately 0.64, or approximately 0.63, or approximately 0.62, or approximately 0.61, or approximately 0.60, or less would be expected. Alternatively, microbial growth and alcohol production may be optimal when acetate is consumed. As such, a $CO2_{produced}/CO_{consumed}$ ratio of >0.667, such as approximately 0.67, or approximately 0.68, or approximately 0.69, or approximately 0.70, or greater would be expected.

Once an optimum level or range has been determined, the fermentation, or future fermentations can be operated under similar conditions, wherein the substrate is supplied such that the experimentally determined carbon fixed and/or $CO2_{produced}/CO_{consumed}$ ratio is substantially maintained. An optimum ratio of fermentation of a substrate comprising CO and H2 can be similarly determined and applied.

In an additional or alternative embodiment, the method can be used to indicate when and/or how a microbial culture can or should be transitioned from one net overall conversion to another. For example, as noted previously, if growth is the primary goal, then the microbial culture may be desirably maintained such that the majority of carbon is directed toward acetate production. For example, a substrate stream comprising CO and minimal or no H2, the $CO2_{produced}/CO_{consumed}$ ratio is maintained around 0.5. If the $CO2_{produced}/CO_{consumed}$ ratio deviates beyond a predetermined range or threshold, such as approximately 0.45-0.55, or approximately 0.48-0.52, an adjustment may be made to the culture and/or the substrate stream to transition at least a portion of the microbial culture such that the overall net conversion by the whole culture is as desired. For example, transition the culture such that the CO2/CO ratio is approximately 0.5. In the presence of H2, equivalent adjustments can similarly be made, such that carbon fixation remains substantially constant.

In particular embodiments of the invention, at least a portion of the microbial culture can be transitioned by making an adjustment to the microbial culture and/or the substrate stream. In certain embodiments, the anaerobic fermentation is carried out in a bioreactor, wherein the microbial culture is at least partially suspended in a fermentation broth comprising a liquid nutrient medium. In particular embodiments, at least a portion of the microbial culture can be transitioned by making an adjustment to the fermentation broth and/or liquid nutrient medium.

In certain embodiments, the adjustment includes one or more of: changing pH of the fermentation broth; changing redox potential of the fermentation broth; changing CO concentration of the fermentation broth; changing H2 concentration of the fermentation broth; changing composition of the substrate stream; changing pressure of the substrate stream; altering fermentation broth agitation rate; product removal; changing acid and/or alcohol concentration of the fermentation broth; changing one or more nutrients in the liquid nutrient medium; changing rate of supply of one or more nutrients.

Additionally or alternatively, if alcohol production is the primary aim then substrate can be provided such that substantially all carbon is fixed as ethanol. In particular embodiments wherein no H2 is available, the $CO2_{produced}/CO_{consumed}$ ratio may be desirably maintained at approx 0.667. If the $CO2_{produced}/CO_{consumed}$ ratio deviates beyond a predetermined range or threshold, such as 0.58-0.73 or 0.63-0.7, an adjustment may be made to the culture and/or the substrate stream to transition at least a portion of the microbial culture such that the overall net conversion by the whole culture is as desired, for example returned to a $CO2_{produced}/CO_{consumed}$ ratio of approx 0.667.

In an additional or alternative embodiment, an alcohol producing culture maintained with a $CO2_{produced}/CO_{consumed}$ ratio of approximately 0.667 may have significant amounts of unwanted acetate, for example residual acetate left from an earlier growth phase. The acetate may be converted to alcohol by transitioning at least a portion of the reduction of acetate to alcohol (equation 3). As such, the culture can be adjusted until the $CO2_{produced}/CO_{consumed}$ ratio increases above 0.667 until the desired conversion is complete.

The proportion of CO oxidised to CO2 can be used to determine the overall net conversion of a microbial culture. The amount of CO consumed by the culture also provides an indication of the viability of the culture (specific uptake: CO uptake rate/cell density). Accordingly, the methods of the invention can be used in combination with specific uptake monitoring. For example, if the proportion of carbon fixed as a particular product and/or the specific uptake deviate from predetermined thresholds or ranges, one or more adjustments can be made to the culture such that viability and desired conversion is maintained. In particular embodiments, wherein H2 is limited or is substantially unavailable, the specific CO uptake is expected to be at least 0.5 mmol/gram dry weight microbial cells/minute (mmol/g/min), such as approximately 0.6 mmol/g/min, such as approximately 0.7 mmol/g/min, such as approximately 0.8 mmol/g/min, such as approximately 0.9 mmol/g/min, such as approximately 1.0 mmol/g/min.

In this regard, the proportion of carbon fixed as a particular product in combination with the specific uptake of CO can be used to determine the rate at which particular desired metabolites, such as acids and/or alcohols, are produced. In particular embodiments, the method can be used to improve the efficiency of the microbial fermentation by optimising (i.e., improving) the rate at which one or more products (such as alcohols) are produced. For example, ethanol production can be improved by making one or more adjustments to the microbial culture that increases the specific uptake of CO while maintaining a $CO2_{produced}/CO_{consumed}$ ratio of approximately 0.667. Additionally or alternatively, one or more adjustments can be made to increase CO uptake and $CO2_{produced}/CO_{consumed}$ ratio from (for example) 0.5 to (for example) 0.667 to improve the rate of alcohol production.

In particular embodiments of the invention, continuous fermentation of substrates comprising CO and optionally H2 can be achieved over extended periods of at least 2 days, such as at least 3 days, or at least 5 days, or at least 1 week, or at least 1 month. Continuous fermentation includes providing fresh media to a fermentation broth and removing fermentation broth containing products and microbial cells to maintain a substantially constant volume fermentation broth. In particular embodiments, the concentrations of products, including alcohol(s) and optionally acid(s) and the microbial cells are maintained substantially constant in the continuous process. In particular embodiments of the invention, to sustain a continuous fermentation over an extended period, the microbial culture fixes at least a portion of carbon as acid, such as acetate. The acetate can be produced at concentration of less than 5 g/L. However, in accordance with the methods of the invention, the majority of the fixed carbon is fixed as alcohol, such as ethanol, in excess of 10 g/L, or 15 g/L. Thus, to maintain continuous operation, the substrate needs to be provided such that carbon is fixed as acetate, ethanol and biomass.

In a particular embodiment, a fermentation producing ethanol and small amounts of acetate continuously over an extended period is maintained within a $CO2_{produced}/CO_{consumed}$ ratio range of approximately 0.61-0.65; such as between 0.62-0.64. Such a $CO2_{produced}/CO_{consumed}$ ratio ensures a majority of fixed carbon is directed toward alcohol production, while a lesser amount is directed toward acetate and cell matter to maintain microbial growth, thus sustaining a continuous culture. In particular embodiments, the substrate is provided such that the specific CO uptake is maintained at least 0.8 mmol/g/min, such as approximately 1.0 mmol/gram dry cell mass/minute.

In accordance with another embodiment, non-continuous (batch) fermentation can be conducted such that alcohol is produced without concomitant acid production. In such embodiments, substrate is supplied such that alcohol and optionally cell matter (biomass) are produced. In accordance with the invention, substrate is provided such that a CO2/CO ratio of approximately 0.667 is maintained. It is recognised that as a microbial culture grows, the amount of CO (and optionally H2) required increases. However, in accordance with the invention, an optimal amount of CO can be provided by maintaining a ratio of CO2/CO as substrate supply rate increases.

Figure 3:
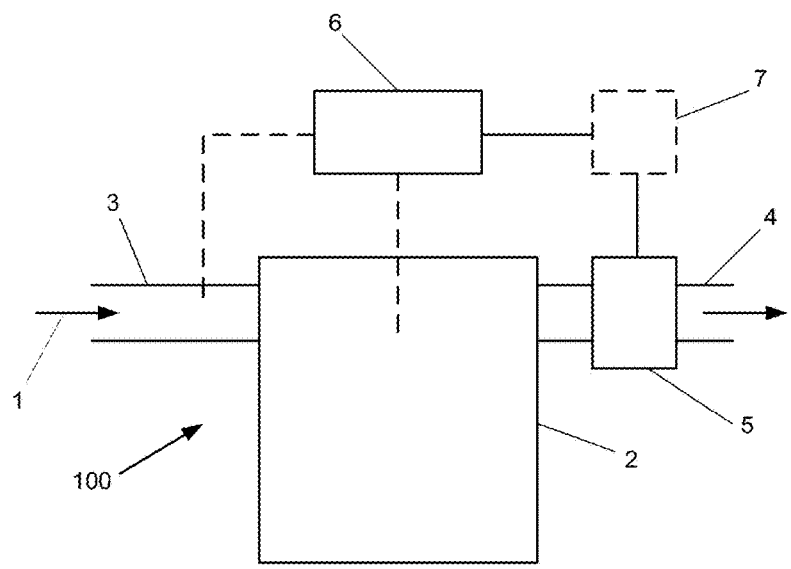
FIG. 3: is a schematic representation of a system including means to determine $CO2_{produced}/CO_{consumed}$ ratio according to certain embodiments of the invention.

FIG. 3 is a schematic representation of a system 100, according to one embodiment of the invention. Substrate stream 1 enters the bioreactor 2 via a suitable conduit 3. Substrate stream 1 comprises CO and optionally CO2 and/or H2 and in certain embodiments, the substrate stream is a waste gas stream from an industrial process, such as the decarburisation of steel. Substrate stream 1 may be a constant stream in the sense that it is constantly supplied, but the content of the stream may vary over time. The composition of the substrate stream, particularly the concentration of CO and CO2 may be known, or may alternatively be determined by optional determining means (not shown).

Bioreactor 2 is configured to perform the desired fermentation reaction to produce products. According to certain embodiments, bioreactor 2 is configured to convert CO into products including one or more acids and/or alcohols. Bioreactor 2 may comprise more than one tank, each tank configured to perform the same reaction and/or different stages within a particular fermentation process and/or different reactions, including different reactions for different fermentations that may include one or more common stages.

The products produced in bioreactor 2, such as acids and/or alcohols, may be recovered by any recovery process known in the art.

Components of the substrate stream that are unconsumed in the fermentation reaction and any by-products of the fermentation reaction, such as CO2, exit bioreactor 2 via exhaust outlet 4. In particular embodiments of the invention, measuring means 5 is adapted to determine the CO, CO2 and optionally H2 concentration in the exhausted stream exiting bioreactor 2 via exhaust outlet 4. In particular embodiments, the proportion of carbon directed to acid(s) and/or alcohol(s) can be determined from the amount of CO, CO2 and H2 supplied to and the amount exiting bioreactor 2. Accordingly, an operator can optionally make adjustments to microbial culture in bioreactor 2 and/or the substrate stream 1 using adjustment means 6 to maintain the microbial culture at, or transition the culture to a desired state of production. Adjustments to maintain or transition the culture includes one or more of: changing pH of the fermentation broth; changing redox potential of the fermentation broth; changing CO concentration of the fermentation broth; changing H2 concentration of the fermentation broth; changing composition of the substrate stream; changing pressure of the substrate stream; fermentation broth agitation rate; product removal; changing acid and/or alcohol concentration of the fermentation broth; changing one or more nutrients in the liquid nutrient medium; changing rate of supply of one or more nutrients.

Additionally or alternatively, system 100 includes optional processing means 7 adapted to determine the proportion of carbon directed toward particular products and control adjustments means 6, such that the culture can be maintained at or transitioned to a desired state.

In particular embodiments, the CO2, H2 and CO entering and/or exiting bioreactor 2 can be monitored continuously or at discrete time point and the carbon fixation determined. Furthermore, adjustment means 6 can be configured to make continuous adjustments or adjustments at discrete time points if necessary.

Any means for determining the $CO2_{produced}/CO_{consumed}$ ratio can be used, however in particular embodiments, one or more gas chromatographs are used to determine CO2 and CO concentrations of the stream exiting the bioreactor 2 and optionally substrate stream 1. In one embodiment, the means for determining the CO and CO2 concentrations in the stream exiting bioreactor 2 is a Varian CP-4900 micro GC.

EXAMPLES

Materials and Methods

Example 1 and 2

| Solution A | |
|---|---|
| $NH_4Ac$ | 3.083 g |
| $MgCl_2 \cdot 6H_2O$ | 0.61 g |
| $CaCl_2 \cdot 2H_2O$ | 0.294 g |
| KCl | 0.15 g |
| NaCl | 0.12 g |
| Distilled Water | Up to 1 L |
| Component/0.1M solution (aq) | Quantity/ml into 1 L media |
| Solution(s) B | |
| $FeCl_3$ | 10 ml |
| $CoCl_2$ | 5 ml |
| $NiCl_2$ | 5 ml |
| $H_3BO_3$ | 1 ml |
| $Na_2SeO_3$ | 1 ml |
| $Na_2MoO_4$ | 1 ml |
| $Na_2WO_4$ | 1 ml |
| $ZnCl_2$ | 1 ml |
| MnCl2 | 1 mL |
| Solution C | |
| Biotin | 20.0 mg |
| Folic acid | 20.0 mg |
| Pyridoxine•HCl | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Litre |
| Solution(s) D | |
| $FeCl_3$ | 2.5 ml |
| $CoCl_2$ | 1.25 ml |
| $NiCl_2$ | 1.2 ml |
| $H_3BO_3$ | 0.25 ml |
| $Na_2SeO_3$ | 0.25 ml |
| $Na_2MoO_4$ | 0.25 ml |
| $Na_2WO_4$ | 0.25 ml |
| $ZnCl_2$ | 0.25 ml |
| MnCl2 | 0.25 mL |

Preparation of Media

Example 1 and 2

Media was prepared as follows: 85% $H_3PO_4$ (20 mmol) was added to a 1 L solution of solution A. The pH of the media was adjusted to 5.3 by the addition of a 5M solution of NaOH. Metal salts were then optionally added according to solution(s) B. The media solution was sterilised by autoclaving for 30 minutes at 121° C., or by filter sterilisation prior to use. Resazurin was added as a redox indicator and 10 ml of B-vitamin Solution (solution C) was added.

Preparation of $Na_2S_x$

A 500 ml flask was charged with $Na_2S$ (93.7 g, 0.39 mol) and 200 ml $H_2O$. The solution was stirred until the salt had dissolved and sulfur (25 g, 0.1 mol) was added under constant $N_2$ flow. After 2 hours stirring at room temperature, the "$Na_2S_x$" solution (approx 4M with respect to [Na] and approx 5M with respect to [S]), now a clear reddish brown liquid, was transferred into $N_2$ purged serum bottles, wrapped in aluminium foil.

Materials and Methods

Examples 3, 4 and 5

| Solution A | |
|---|---|
| $NH_4Ac$ | 3.083 g |
| $MgCl_2 \cdot 6H_2O$ | 0.61 g |
| Distilled Water | |
| $CaCl_2 \cdot 2H_2O$ | 0.294 g |
| KCl | 0.15 g |
| Up to 1 L | |

-continued

| Component | Mol/L H2O |
|---|---|
| Solution(s) B | |
| FeCl$_3$ | 0.1 |
| CoCl$_2$ | 0.05 |
| NiCl$_2$ | 0.05 |
| H$_3$BO$_3$ | 0.01 |
| Na$_2$SeO$_3$ | 0.01 |
| Na$_2$MoO$_4$ | 0.01 |
| ZnCl$_2$ | 0.01 |
| MnCl2 | 0.01 |
| Solution C | |
| Biotin | 20.0 mg |
| Folic acid | 20.0 mg |
| Pyridoxine•HCl | 10.0 mg |
| Thiamine•HCl | 50.0 mg |
| Riboflavin | 50.0 mg |
| Distilled water | |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| To 1 Litre | |

Preparation of Cr (II) Solution

A 1 L three necked flask was fitted with a gas tight inlet and outlet to allow working under inert gas and subsequent transfer of the desired product into a suitable storage flask. The flask was charged with CrCl$_3$.6H$_2$O (40 g, 0.15 mol), zinc granules [20 mesh] (18.3 g, 0.28 mol), mercury (13.55 g, 1 mL, 0.0676 mol) and 500 mL of distilled water. Following flushing with N$_2$ for one hour, the mixture was warmed to about 80° C. to initiate the reaction. Following two hours of stirring under a constant N$_2$ flow, the mixture was cooled to room temperature and continuously stirred for another 48 hours by which time the reaction mixture had turned to a deep blue solution. The solution was transferred into N$_2$ purged serum bottles and stored in the fridge for future use.

Bacteria:

*Clostridium autoethanogenum* used is that deposited at the German Resource Centre for Biological Material (DSMZ) and allocated the accession number DSMZ 19630.

Sampling and Analytical Procedures

Media samples were taken from the CSTR reactor at intervals over periods up to 20 days. Each time the media was sampled care was taken to ensure that no gas was allowed to enter into or escape from the reactor.

HPLC:

HPLC System Agilent 1100 Series. Mobile Phase: 0.0025N Sulfuric Acid. Flow and pressure: 0.800 mL/min. Column: Alltech 10A; Catalog #9648, 150×6.5 mm, particle size 5 µm. Temperature of column: 60° C. Detector: Refractive Index. Temperature of detector: 45° C.

Method for Sample Preparation:

400 µL of sample and 50 µL of 0.15M ZnSO$_4$ and 50 µL of 0.15M Ba(OH)$_2$ are loaded into an Eppendorf tube. The tubes are centrifuged for 10 min. at 12,000 rpm, 4° C. 200 µL of the supernatant are transferred into an HPLC vial, and 54 are injected into the HPLC instrument.

Headspace Analysis:

Measurements were carried out on a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Example 1

Batch Fermentation in CSTR 1.5 liters of the media solution containing solution(s) B was aseptically and anaerobically transferred into a 2 L CSTR vessel, and continuously sparged with N$_2$. Once transferred to the fermentation vessel, the reduction state and pH of the transferred media could be measured directly via probes. The media was heated to 37° C. and stirred at 300 rpm. The media was then reduced further to −130 mV by the addition of 0.3M Cr(II)chloride solution.

Polysulfide solution (0.1% v/v, 1.5 mL) was added to the solution, and a black precipitate was observed in the media. An initial drop in potential to −300 mV was also observed, which stabilised to −150 mV over several hours. N$_2$ was continuously sparged through the solution following the addition of the polysulfide solution.

Prior to inoculation, the gas was switched to a pre-mixed blend of 70% CO, 1% H$_2$, 15% CO2, and 14% N$_2$, which was continuously sparged into the fermentation broth throughout the experiment. An actively growing *Clostridium autoethanogenum* culture was inoculated into the CSTR at a level of approximately 7.5% (v/v). During this experiment, the pH was maintained at approximately 5.5.

Results:

A comparison between metabolite production and the $CO2_{produced}/CO_{consumed}$ ratio can be seen in FIG. 1. After a lag period during which the culture consumed no significant quantity of gas, gas consumption and metabolite production commenced after around 5 days.

For the first three days the $CO2_{produced}/CO_{consumed}$ ratio remained between 0.55 and 0.62, a value at which the model implies ethanol will be produced co-currently with acetate; an increase in both ethanol and acetate is observed via HPLC analysis at the same time.

At day nine the $CO2_{produced}/CO_{consumed}$ spikes to 0.66, a value projected by the model to be indicative of nearly all uptake carbon being directed into ethanol production with little or no acetate production. HPLC analysis from this same day shows continuing ethanol production by the culture, but the levelling off of acetate levels. A slightly higher ratio would indicate acetate consumption, an event observed to have occurred in the overnight period between days 11 and 12 from HPLC analysis when gas headspace analysis was not carried out.

On days 12 and 13, the ratio moves closer to 0.6, indicating continued ethanol production with some acetate production; again, an observation matched by HPLC measurements. From days 14 through 16, the ratio rises over 0.667, indicating ethanol production from acetate consumption. HPLC data from these days shows continued ethanol accumulation, but fluctuating acetate levels, with minor increases and decreases. On day 19 the ratio has fallen drastically to below 0.5, suggesting ethanol consumption, with HPLC analysis for the period showing a reduction in ethanol concentration. After day 19 gas consumption by the reactor was close to zero and the culture was presumed to be inactive.

Example 2

Batch Fermentation in CSTR 1.5 liters of the media solution without solution(s) B, was aseptically and anaerobically transferred into a 2 L CSTR vessel, and continuously sparged with $N_2$. Once transferred to the fermentation vessel, the reduction state and pH of the transferred media could be measured directly via probes. The media was heated to 37° C. and stirred at 300 rpm. The media was then reduced further to −130 mV by the addition of 0.3M Cr(II)chloride solution.

Polysulfide solution (3M solution, 1.0 mL) was added to the solution. An initial drop in potential to −220 mV was also observed, which stabilised to −100 mV over several hours. Following 12 hours continuous sparging with $N_2$, solution(s) D was added to the solution and the ORP adjusted to approx −200 mV by addition of Cr(II).

Prior to inoculation, the gas was switched to a pre-mixed blend of 70% CO, 1% $H_2$, 15% $CO_2$, and 14% $N_2$, which was continuously sparged into the fermentation broth throughout the experiment. An actively growing *Clostridium autoethanogenum* culture was inoculated into the CSTR at a level of approximately 7.5% (v/v). During this experiment, the pH was not externally controlled.

Figure 2:
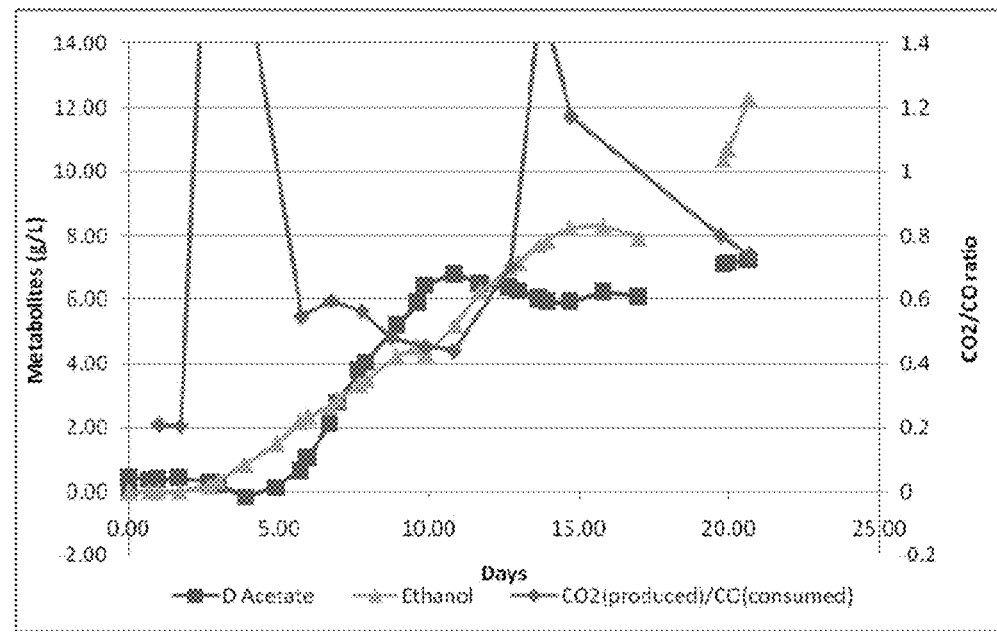
FIG. 2: is a graph showing changes in acetate and alcohol production and $CO2_{produced}/CO_{consumed}$ in a batch fermentation of a substrate comprising CO to produce products including alcohol.

Results:

A comparison between metabolite production and the $CO2_{produced}/CO_{consumed}$ ratio can be seen in FIG. 2. After a lag period during which the culture consumed no significant quantity of gas, gas consumption and metabolite production commenced around day 3. Initially the $CO2_{produced}/CO_{consumed}$ is observed to be very high, in fact, over 1:1. Calculated values over 1:1 are treated by the model as being equal to 1:1. A ratio this high suggests consumption of acetate and production of ethanol. HPLC analysis in this time period showed a corresponding decrease in the levels of acetate and an increase in ethanol. Between day 5 and 9, the ratio falls between 0.6 and 0.5, indicating ethanol production co-current with acetate production, in agreement with the HPLC analysis. Between days 8 and 11 the $CO2_{produced}/CO_{consumed}$ ratio falls below 0.5, indicating ethanol consumption. On days 9 and 10 HPLC analysis shows a drop in ethanol concentration. After day 11 the ratio rises above 0.667, indicating ethanol production from acetate consumption, in agreement with the observed decrease in acetate from HPLC analysis. This consumption becomes more pronounced on days 13 and 14, with a corresponding jump in the ratio above 1:1.

During a period from day 15 to day 18, no gas headspace was carried out, although HPLC analysis shows a gradual decrease in ethanol levels and a slight increase in acetate.

On day 19 when head space analysis was resumed, the ratio was above 0.667, indicating ethanol production and acetate consumption. HPLC analysis showed ethanol levels had risen markedly during the period where no sampling had been carried out, but acetate levels were remaining more or less static. No further data collection was carried out on the culture after day 20.

Example 3

Batch Fermentation in CSTR

Media was prepared as follows: 85% $H_3PO_4$ (45 mmol) was added to a 1.5 L solution of solution A. The pH of the media was adjusted to 5.3 by the addition of a 5M solution of NaOH. The media solution was sterilised by autoclaving for 30 minutes at 121° C., or by filter sterilisation prior to use. Resazurin was added as a redox indicator. The media solution was aseptically and anaerobically transferred into a 1.5 L CSTR vessel, and continuously sparged with $N_2$. Once transferred to the fermentation vessel, the reduction state and pH of the transferred media could be measured directly via probes. The media was heated to 37° C. and stirred at 300 rpm.

Sodium sulfide solution (3.75 mL of a 0.2M solution) was added, followed by nitriloacetic acid (1.5 mL of a 0.1M solution), trace metal solution B (1.5 mL) Na2WO4 (1.5 mL of a 0.01M solution) then B-Vitamin Solution C (15 mL). ORP of the solution was adjusted to approx −200 mV using Cr(II) solution.

Prior to inoculation, the gas was switched to a blend of 33% H2, 23% N2, 31% $CO_3$ 13% CO2.

An actively growing *Clostridium autoethanogenum* culture was inoculated into the CSTR at a level of approximately 10% (v/v). During this experiment, the pH was maintained at approximately 5.3 and Na2S solution was added at a rate of approx 0.16 mMol/day.

Figure 4:
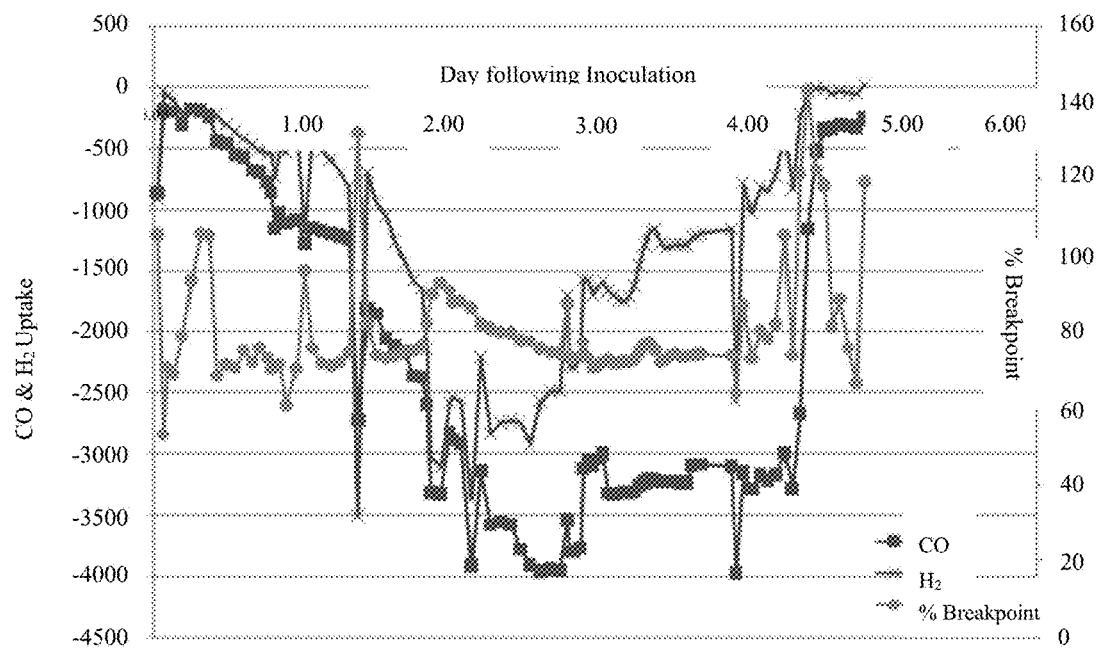
FIG. 4: is a graph showing the amount of CO and H2 consumed by a microbial culture from example 3.
Figure 5:
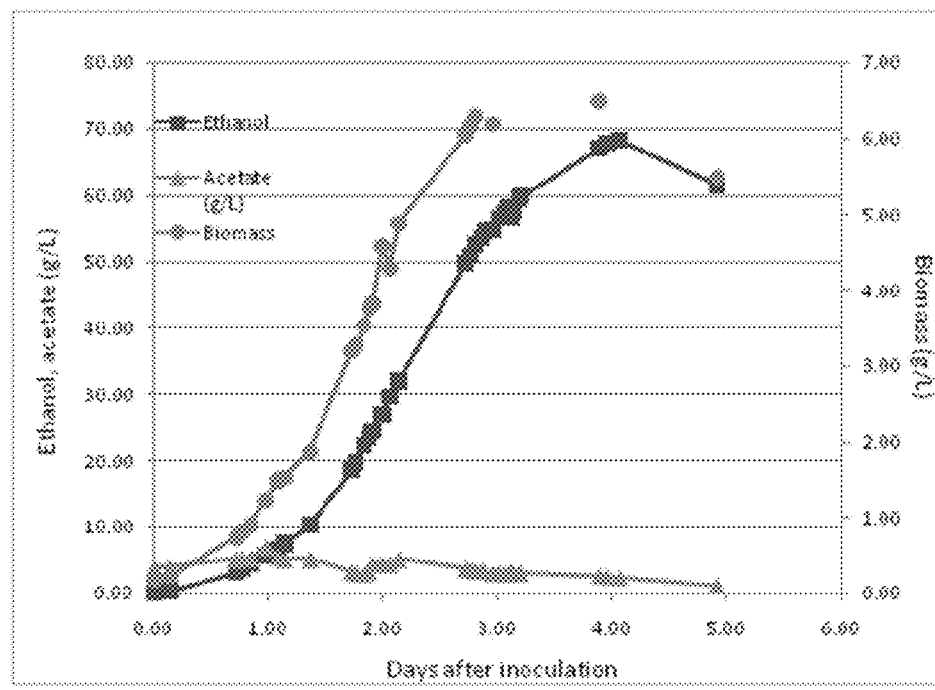
FIG. 5: is a graph showing metabolite production and growth of a microbial culture from example 3.

The gas supply and agitation were increased over the time course of the fermentation in response to changes in the gas stream exiting the bioreactor. In accordance with the methods of the invention, the proportion of carbon directed to alcohol was maintained at a high level by maintaining a breakpoint of greater than 70% but less than 100%. CO, H2 uptake and breakpoint are displayed in FIG. 4, while microbial growth and metabolite production are shown in FIG. 5. By maintaining substrate supply at a level to promote alcohol production, no acetate is produced, while ethanol and biomass accumulate rapidly.

Example 4

Batch Fermentation in CSTR

Media was prepared as follows: 85% $H_3PO_4$ (45 mmol) was added to a 1.5 L solution of solution A. The pH of the media was adjusted to 5.3 by the addition of a 5M solution of NaOH. The media solution was sterilised by autoclaving for 30 minutes at 121° C., or by filter sterilisation prior to use. Resazurin was added as a redox indicator. The media solution was aseptically and anaerobically transferred into a 1.5 L CSTR vessel, and continuously sparged with $N_2$. Once transferred to the fermentation vessel, the reduction state and pH of the transferred media could be measured directly via probes. The media was heated to 37° C. and stirred at 300 rpm.

Sodium sulfide solution (3.75 mL of a 0.2M solution) was added, followed by nitriloacetic acid (1.5 mL of a 0.1M solution), trace metal solution B (1.5 mL) Na2WO4 (1.5 mL of a 0.01M solution) then B-Vitamin Solution C (15 mL). ORP of the solution was adjusted to approx −200 mV using Cr(II) solution.

Prior to inoculation, the gas was switched to a blend of 50% CO and 50% N2, which was continuously sparged into the fermentation broth throughout the experiment. An actively growing *Clostridium autoethanogenum* culture was inoculated into the CSTR at a level of approximately 10% (v/v). During the fermentation, the pH was maintained at approximately 5.3 and Na2S solution was added at a rate of approx 0.16 mMol/day.

Figure 6:
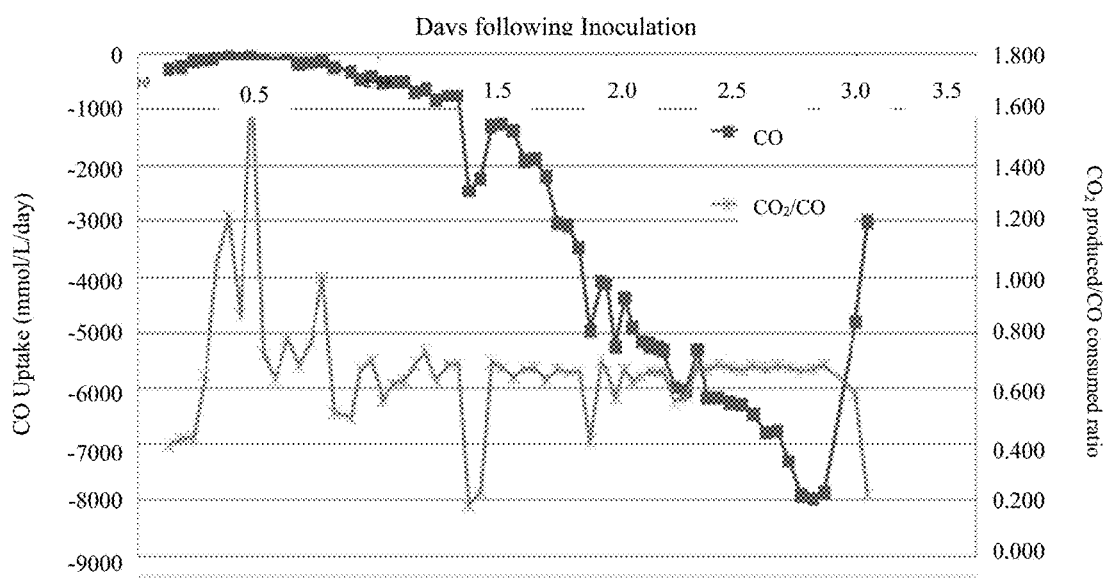
FIG. 6: is a graph showing the amount of CO and consumed by a microbial culture from example 4.
Figure 7:
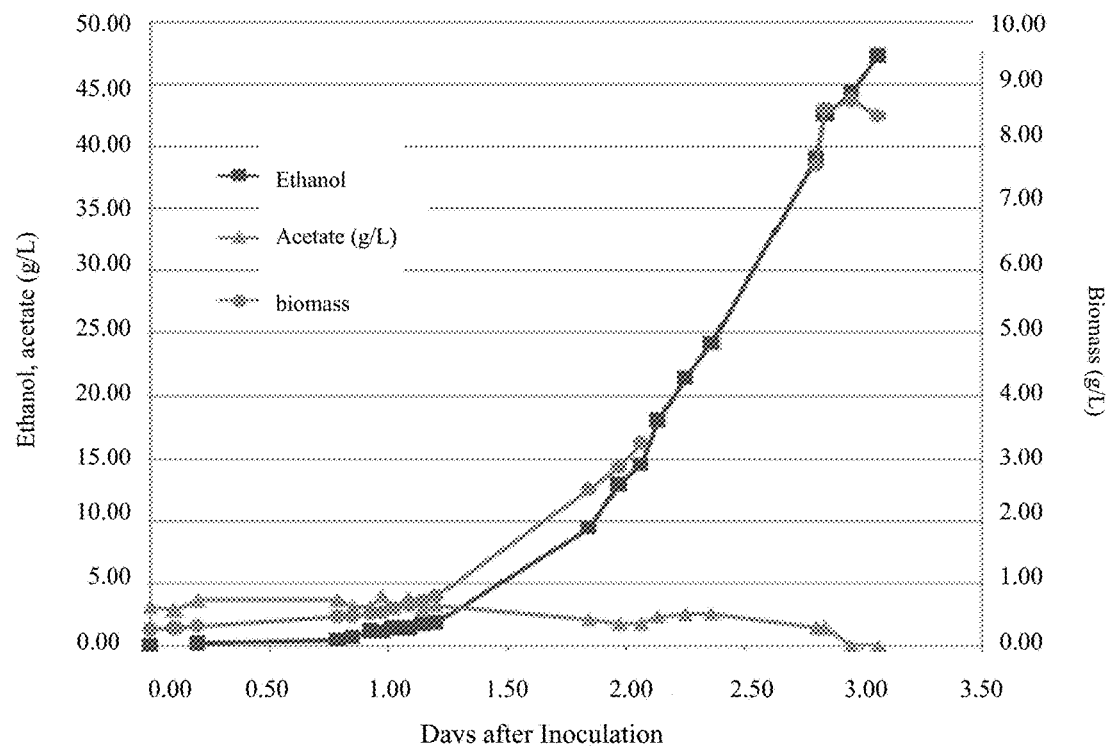
FIG. 7: is a graph showing metabolite production and growth of a microbial culture from example 4.

The gas supply and agitation were increased over the time course of the fermentation in response to changes in the gas stream exiting the bioreactor. In accordance with the methods of the invention, $CO2_{produced}/CO_{consumed}$ ratio was maintained at approximately 0.667 such that substantially all carbon is directed to alcohol production. CO uptake and $CO2_{produced}/CO_{consumed}$ ratio are displayed in FIG. 6, while microbial growth and metabolite production are shown in FIG. 7. By maintaining substrate supply at a level to promote alcohol production, no acetate is produced, while ethanol and biomass accumulate rapidly.

Example 5

Continuous Fermentation in CSTR

A 2 L CSTR was set up under the following conditions: Media was prepared as follows: 85% $H_3PO_4$ (30 mM) was added to 1.5 L of solution A. The pH of the media was adjusted to 5.3 by the addition of NH4OH. The media solution was sterilised by autoclaving for 30 minutes at 121° C., or by filter sterilisation prior to use. Resazurin was added as a redox indicator. The media solution was aseptically and anaerobically transferred into a 1.5 L CSTR vessel, and continuously sparged with $N_2$. Once transferred to the fermentation vessel, the reduction state and pH of the transferred media could be measured directly via probes. The media was heated to 37° C. and stirred at 300 rpm, then trace metal solution B including 0.3 Mol/L nitriloactetic acid (1.5 mL), then Na2WO4 (1.5 mL of a 0.01M solution) then Solution C (15 mL) were added. Prior to inoculation, the gas was switched to 2% H2, 28% N2, 48% $CO_3$ and 22% CO2. An actively growing *Clostridium autoethanogenum* culture was inoculated into the CSTR at a level of approximately 10% (v/v). During this experiment, Na2S (0.2M) solution was added at a rate of approx 0.3 ml/hour.

The microbial culture was allowed to grow in batch mode for approximately 1 day. At day 1, the fermentation was switched to continuous operation wherein fresh media was provided to achieve a dilution rate of approximately 1 to 1.8. Substrate supply was increased in response to the requirements of the microbial culture.

Figure 8:
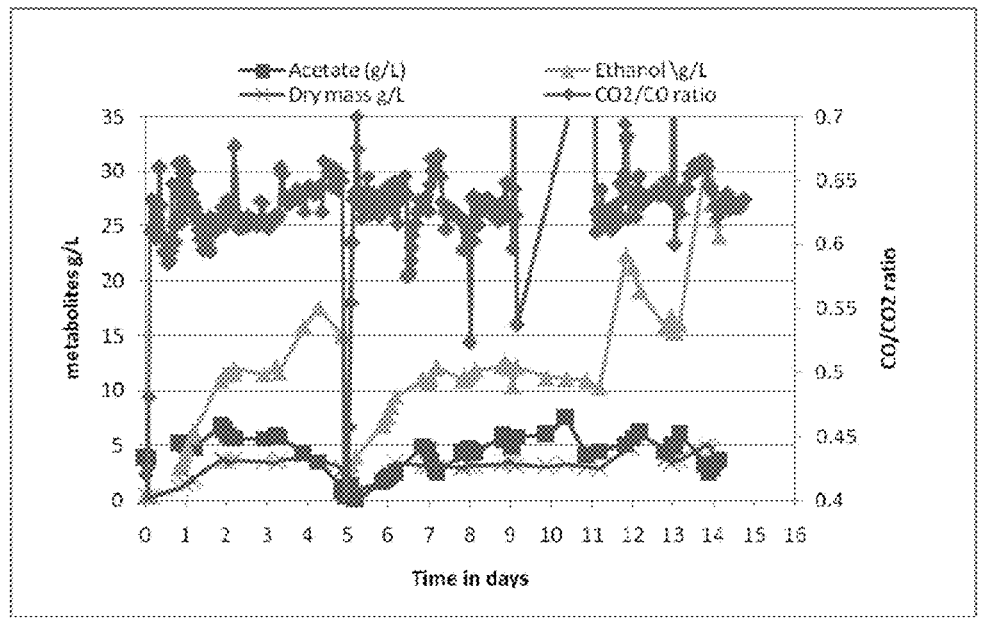
FIG. 8: is a graph showing metabolite production in a continuous fermentation from example 5.

Results of the fermentation are shown in FIG. 8. The substrate supply rate and agitation rate were increased or decreased over the time course of the fermentation in response to changes in the proportion of CO converted to CO2. In accordance with the invention, sustainable continuous operation was achieved by maintaining a CO2/CO ratio of approximately 0.62-0.64. Sustainable continuous operation resulted in a stable biomass of approximately 3 g/L, substantially stable acetate concentration of approximately 5 g/L and substantially stable ethanol concentration of at least 10 g/L. The specific CO uptake by the microbial culture was maintained approximately 1.0 mmol/g/min.

Example 6

Prophetic

Fermentation of a substrate comprising CO by an carboxydotrophic microbial culture comprising in liquid nutrient medium, wherein the conditions (such as those well known in the art) promote rapid growth of the culture with concomitant production of acetate. Under such conditions, $CO2_{produced}/CO_{consumed}$ ratio will optimally be maintained at approximately 0.5. However, at a stage when an operator desires to switch the culture from acetate production to alcohol production, one or more adjustments can be made. In particular embodiments, the pH of the liquid nutrient medium can be decreased such that at least a portion of the microbial culture is transitioned to a state where alcohol is produced. As the desired transition is made the $CO2_{produced}/CO_{consumed}$ ratio will increase toward approximately 0.667. In another embodiment, rather than manually altering the pH, the adjustment may be brought about by ceasing control of pH such that the microbial culture can self regulate pH.

Example 7

Prophetic

Fermentation of a substrate comprising CO by a carboxydotrophic microbial culture in liquid nutrient medium, wherein the conditions (such as those well known in the art) promote alcohol production. Under such conditions, the $CO2_{produced}/CO_{consumed}$ ratio will optimally be maintained at approximately 0.667. However, if the $CO2_{produced}/CO_{consumed}$ ratio deviates from this value, for example dropping to approximately 0.5, one or more adjustments can be made to increase the ratio back toward the optimum value. For example, the hydrogen component of the gas stream can be increased such that alcohol production is promoted.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, heading, or the like are provided to enhance the reader's comprehension of this document, and should not be read as limiting the scope of the present invention. The entire disclosures of all applications, patents and publications cited above and below, if any, are herein incorporated by reference.

The reference to any prior art in this specification is not, and should not be taken as, an acknowledgement or any form of suggestion that that prior art forms part of the common general knowledge in the field of endeavour in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method of improving the efficiency of microbial fermentation of a gaseous substrate comprising CO and less than 5% $H_2$, said method comprising: a) providing the substrate to a microbial culture comprising one or more micro-organism to produce products selected from the group consisting of acids, alcohols and mixtures thereof and $CO_2$ as a by-product; b) measuring the total amount of CO consumed by the microbial culture and the amount of $CO_2$ produced by the microbial culture and calculating a ratio of $CO_2{}_{produced}/CO_{consumed}$; c) adjusting the substrate supply rate to keep the $CO_2{}_{produced}/CO_{consumed}$ ratio within a predetermined range of a value of the ratio of about 0.5 to optimize acid production or about 0.667 to optimize ethanol production; and d) repeating steps b and c to keep the $CO_2{}_{produced}/CO_{consumed}$ ratio within the predetermined range.

2. The method of claim 1 where the substrate supply rate is:
   a) increased if the ratio of $CO_2{}_{produced}/CO_{consumed}$ is below the predetermined range of the value of the ratio;
   b) decreased if the ratio of $CO_2{}_{produced}/CO_{consumed}$ is above the predetermined range of the value of the ratio;
   c) maintained if the ratio of $CO_2{}_{produced}/CO_{consumed}$ is within the predetermined range of the value of the ratio.

3. The method of claim 2, further comprising automatically adjusting the substrate supply rate such that the $CO_{2\ produced}/CO_{cosumed}$ ratio is maintained within the predetermined range.

4. The method of claim 1 where the fermentation is carried out by a micro-organism selected from the group consisting of *Clostridia, Moorella, Eubacterium, Desulfobacterium, Carboxydothermus, Acetobacterium*, and *Butyribacterium*.

5. The method of claim 4 where the *Clostridia* micro-organism is *Clostridium autoethanogenum*.

6. A method of improving the efficiency of microbial fermentation of a gaseous substrate comprising CO and less than 5% H2, said method comprising: a) providing the substrate to a microbial culture comprising one or more micro-organism to produce products selected from the group consisting of acids, alcohols and mixtures thereof and $CO_2$ as a by-product; b) measuring the total amount of CO consumed by the microbial culture and the amount of $CO_2$ produced by the microbial culture and determining a desired ratio of $CO_{2\ produced}/CO_{consumed}$; c) adjusting the substrate supply rate to keep the $CO_2$ produced/$CO_{consumed}$ ratio within a predetermined range of the desired ratio; and d) repeating steps (b) and (c) to keep the $CO_{2\ produced}/CO_{consumed}$ ratio within the predetermined range, wherein the ratio of $CO_{2\ produced}/CO_{consumed}$ is about 0.5 to optimize acid production and about 0.667 to optimize ethanol production.

7. The method of claim 6 where the substrate supply rate is:
  a) increased if the ratio of $CO_{2\ produced}/CO_{consumed}$ is below the predetermined range of the desired ratio;
  b) decreased if the ratio of $CO_{2\ produced}/CO_{cousumed}$ is above the predetermined range of the desired ratio;
  c) maintained if the ratio of $CO_{2\ produced}/CO_{consumed}$ is within the predetermined range of the desired ratio.

8. The method of claim 7 further comprising automatically adjusting the substrate supply rate such that the $CO_{2\ produced}/CO_{cousumed}$ ratio is maintained within the predetermined range.

9. The method of claim 6 where the fermentation is carried out by a micro-organism selected from the group consisting of *Clostridia, Moorella, Eubacterium, Desulfobacterium, Carboxydothermus, Acetobacterium*, and *Butyribacterium*.

10. The method of claim 9 where the Clostridia micro-organism is *Clostridium autoethanogenum*.

* * * * *